(12) United States Patent
Brown (10) Patent No.: US 8,533,292 B2
(45) Date of Patent: Sep. 10, 2013

(54) SYSTEM AND METHOD FOR MODIFYING DOCUMENTS SENT OVER A COMMUNICATION NETWORK

(75) Inventor: Stephen J. Brown, Woodside, CA (US)

(73) Assignee: Robert Bosch GmbH, Stuttgart (DE)

( * ) Notice: Subject to any disclaimer, the term of this patent is extended or adjusted under 35 U.S.C. 154(b) by 1150 days.

(21) Appl. No.: 11/613,720

(22) Filed: Dec. 20, 2006

(65) Prior Publication Data

US 2007/0094353 A1  Apr. 26, 2007

Related U.S. Application Data

(63) Continuation of application No. 11/301,331, filed on Dec. 13, 2005, now Pat. No. 7,814,143, which is a continuation of application No. 09/540,482, filed on Mar. 31, 2000, now abandoned, which is a continuation of application No. 09/394,219, filed on Sep. 13, 1999, now Pat. No. 6,375,469, which is a continuation of application No. 08/814,293, filed on Mar. 10, 1997, now Pat. No. 5,951,300, which is a continuation of application No. 08/784,270, filed on Jan. 15, 1997, now Pat. No. 5,887,133.

(51) Int. Cl.
*G06F 15/16* (2006.01)

(52) U.S. Cl.
USPC ........... 709/219; 715/204; 715/236; 715/238; 715/253; 715/271; 705/14.66

(58) Field of Classification Search
USPC .................. 709/203, 217–219; 707/1, 2, 10; 705/1–4; 600/300; 434/262
See application file for complete search history.

(56) References Cited

U.S. PATENT DOCUMENTS

| | | | |
|---|---|---|---|
| 5,304,112 A | | 4/1994 | Mrklas et al. |
| 5,307,263 A | | 4/1994 | Brown |
| 5,528,492 A | * | 6/1996 | Fukushima ............... 707/1 |
| 5,577,189 A | * | 11/1996 | Gay et al. ............... 715/800 |
| 5,664,208 A | * | 9/1997 | Pavley et al. ............ 715/209 |
| 5,710,918 A | | 1/1998 | Lagarde et al. |
| 5,734,915 A | * | 3/1998 | Roewer ................ 715/202 |
| 5,749,083 A | | 5/1998 | Koda et al. |
| 5,784,562 A | * | 7/1998 | Diener ................. 709/217 |
| 5,787,295 A | | 7/1998 | Nakao |
| 5,793,368 A | * | 8/1998 | Beer .................. 715/747 |
| 5,794,251 A | | 8/1998 | Watanabe et al. |
| 5,799,318 A | | 8/1998 | Cardinal et al. |
| 5,802,299 A | * | 9/1998 | Logan et al. ........... 709/218 |
| 5,802,518 A | * | 9/1998 | Karaev et al. ........... 707/9 |
| 5,802,534 A | | 9/1998 | Hatayama et al. |
| 5,806,057 A | | 9/1998 | Gormley et al. |

(Continued)

*Primary Examiner* — Greg C Bengzon
(74) *Attorney, Agent, or Firm* — Maginot, Moore & Beck (57) ABSTRACT

A system and method applied to a communications network which transmits document portions in which an original document portion having an identifier portion and an information portion is replaced or swapped with a substitute document portion. The system has a controller, typically a proxy server, for reading the identifier portion of the original document portion, determining the information portion of the original document portion, and issuing a swap order when an undesired original document portion is found. A substitute document server receives the swap order and sends the substitute document portion to the controller. A swapping device or mechanism inserts the substitute document portion in place of the original document portion and the substitute document portion is passed on to the user set and displayed. The controller and swapping mechanism can be integrated with the user set or with the resources of the service provider and their functionality can reside in software.

39 Claims, 6 Drawing Sheets

(56) References Cited

U.S. PATENT DOCUMENTS

| | | | | |
|---|---|---|---|---|
| 5,845,084 A | * | 12/1998 | Cordell et al. | 709/234 |
| 5,867,821 A | * | 2/1999 | Ballantyne et al. | 705/2 |
| 5,879,163 A | | 3/1999 | Brown et al. | |
| 5,895,461 A | * | 4/1999 | De La Huerga et al. | 707/1 |
| 5,897,644 A | * | 4/1999 | Nielsen | 715/210 |
| 5,926,825 A | * | 7/1999 | Shirakawa | 715/273 |
| 5,951,300 A | | 9/1999 | Brown | |
| 5,956,737 A | * | 9/1999 | King et al. | 715/202 |
| 5,987,480 A | * | 11/1999 | Donohue et al. | 715/207 |
| 6,014,630 A | * | 1/2000 | Jeacock et al. | 705/3 |
| 6,029,182 A | * | 2/2000 | Nehab et al. | 715/205 |
| 6,108,637 A | * | 8/2000 | Blumenau | 715/204 |
| 6,161,114 A | * | 12/2000 | King et al. | 715/202 |
| 6,178,432 B1 | * | 1/2001 | Cook et al. | 715/201 |
| 6,225,993 B1 | * | 5/2001 | Lindblad et al. | 715/716 |
| 6,230,173 B1 | * | 5/2001 | Ferrel et al. | 715/205 |
| 6,308,198 B1 | * | 10/2001 | Uhler et al. | 709/200 |
| 6,345,268 B1 | * | 2/2002 | de la Huerga | 707/3 |
| 6,544,295 B1 | * | 4/2003 | Bodnar | 709/219 |
| 6,589,292 B1 | * | 7/2003 | Langford-Wilson | 715/210 |
| 6,611,862 B2 | | 8/2003 | Reisman | 709/217 |
| 6,820,093 B2 | * | 11/2004 | de la Huerga | 707/104.1 |
| 6,928,609 B2 | * | 8/2005 | Bricklin et al. | 715/205 |
| 7,136,853 B1 | * | 11/2006 | Kohda et al. | 707/6 |
| 7,305,472 B2 | * | 12/2007 | Mighdoll et al. | 709/226 |
| 7,461,332 B2 | * | 12/2008 | Brintzenhofe et al. | 715/205 |
| 8,027,874 B2 | * | 9/2011 | Angles et al. | 705/14.4 |
| 8,108,899 B2 | * | 1/2012 | Shoff et al. | 725/52 |
| 2002/0056136 A1 | * | 5/2002 | Wistendahl et al. | 725/135 |

* cited by examiner

SYSTEM AND METHOD FOR MODIFYING DOCUMENTS SENT OVER A COMMUNICATION NETWORK

RELATED APPLICATION DATA

This invention is a continuation of Ser. No. 11/301,331 filed on Dec. 13, 2005, now U.S. Pat. No. 7,814,143 which is a continuation of Ser. No. 09/540,482 filed on Mar. 31, 2000, now abandoned, which is a continuation of Ser. No. 09/394,219, filed on Sep. 13, 1999, now U.S. Pat. No. 6,375,469, which is a continuation of Ser. No. 08/814,293 filed on Mar. 10, 1997, now U.S. Pat. No. 5,951,300, which is a continuation of Ser. No. 08/784,270, filed Jan. 15, 1997, now U.S. Pat. No. 5,887,133, each of which is incorporated by reference in its entirety.

FIELD OF THE INVENTION

The present invention relates generally to modifying documents sent over a communications network, and in particular to a system and method for determining the information contents of document portions and replacing undesired document portions with substitute document portions or inserting substitute document portions.

BACKGROUND OF THE INVENTION

To a large degree, the information age has been brought about by rapid advances in the field of communications and communications networks in particular. Increasingly, information which could formerly be presented in tangible, permanent media is reformatted and rendered for display on screens and monitors. Virtually any information presentable as text or text and graphics is being converted into suitable electronic messages or packets for shuttling across a communications network.

A communications network, e.g., the Internet, has an architecture in which information packets from resources or content providers is made available through service providers to users who subscribe to the service. The actual transmission takes place over the communication links of various bandwidths and types which make up the network. Content providers typically store this electronic data on server machines connected directly to the Internet in standard format. The data is broken down into packets and these are then transmitted over the communication link. Among the diverse types of information which may be placed on the Internet in this way are articles, news briefs and updates, weather maps, books, summaries, files, software, catalogues, documents, pictorials, video files, public records, commercial literature and so forth.

Clearly, the number of packets which can be transmitted via a communications network is vast and varied. To aid in sorting, routing and transmitting information on the Internet the content of any given packet is usually identified by its origin (address of the content provider), a brief summary located in a conspicuous portion of the packet (e.g., in the header) or some other identification information. For example, the Internetwork Packet Exchange (IPX) protocol followed by NetWare routers, distributed by Novell, Inc., execute a so-called Routing Information Protocol (RIP) and Service Advertising Protocol (SAP). The RIP protocol involves periodic RIP broadcast packets containing all routing information known to the router. These packets are used to keep the global network synchronized. In addition, the protocol provides for periodically sending SAP broadcast packets containing all server information known to the SAP agent. Thus, the network system keeps track of the contents of the various packets to facilitate transfer, mitigate traffic problems and perform other vital operations.

In U.S. Pat. No. 5,530,852 issued to Meske, Jr. et al. the inventors disclose a method and system for receiving information in a first file written in a first markup language and identifying the information contents. The method and system ensure that even complex packets of information are processed by generating a list of profiles and topics for each list of the profiles. Secondary and tertiary files are created with anchors referencing particular information in the first file. A parsing procedure is taught by Meske to ascertain whether any information in the first file (original packet) is relevant. If so, fourth and fifth files containing the desired information are created and sent to the user.

Meske's system and method can be adapted to block or filter entire packets or portions thereof on a content-basis before performing the necessary steps to display the information—usually in the form of a page—on the user's screen. The document is later parsed to extract the profile and build additional pages to catalog and access the information. This method for building a knowledge base with embedded content profiles and in a document is useful but limited to processing the received information only.

The above-mentioned IPX protocol and similar methods which determine the information contents of packets and use them in the routing process can be employed to control the transfer of packets. For example, U.S. Pat. No. 5,541,911 issued to Nilakantan et al. discloses a remote smart filtering communication management system which uses the information contents data to alleviate network traffic problems.

In particular, Nilakantan controls the traffic across a communication link between a remote network and a central device by applying forwarding rules. The resources monitor the characteristics of the forwarded data packets received across the communication link to learn characteristics of the users of the remote network. In response to the learned characteristics, the resources generate link management messages and forward these to the remote interface. The remote link management resources in the remote interface are responsive to the link management messages and tailor the forwarding rules to the user characteristics. The packets can now be filtered or blocked based on user characteristics.

The use of selective blocking and filtering of packets by Nilakantan et al. is applied to ultimately reduce network traffic. The invention is centered around sending management messages which are then used to optimize packet traffic across given links in the network. In other words, the problem addressed by this invention is the high volume caused by the proliferation of packets on the network.

Blocking and filtering of packets or their parts can be employed to speed up the page rendering process on the user's screen. For example, blocking functions may restrict packets from a list of providers or an entire block of providers from ever being sent to the user. This feature allows one to prevent undesired packets (e.g., packets containing adult material) from being sent to the user and rendered on his or her screen. Filters can be preset to chose packets based on the time they require for rendering or in accordance with other user-specified standards (e.g., information contents). Proper application of these two functions results in an optimized and personalized page rendering procedure.

In the most common practical scenario, however, a network user sends a direct request for an entire document from a terminal located on his or her premises to the service provider. The provider verifies whether the document is already stored in local memory and, if not, obtains this document from the content provider. While the user's request is processed the service provider usually passes on to the user a number of unsolicited document portions, e.g., document portions from other service providers such as advertisement servers. Thus, the subscriber receives, in addition to the requested document(s), numerous other document portions of varying degrees of interest or importance to him or her. When the page is rendered on the user's screen these embedded document portions are displayed as a part of the document.

Under these circumstances, what is needed is a system and method for modifying or substituting undesired document portions rather than performing blocking and filtering functions on the packet level. For example, the service provider, the user or another party may wish to exchange or modify a document being sent to the user. This situation may occur when the service provider wishes to enclose vital information with the document requested by the user. The use of the bandwidth allocated to a less important document portion, hence a document portion swap, would be highly appropriate for this purpose. In another situation, the user may wish to block undesired document portions. For instance, when recording television programming on the VCR recorder the user can selectively block advertising material from being recorded. Analogously, when rendering a web page the user may wish to omit specific document portions from being rendered on the page.

At the present time the problems associated with this type of document modification have not been addressed, much less solved. Consequently, what is needed is a system and method which solves the problems associated with document modification based on the information contents in a communications network such as the Internet.

OBJECTS AND ADVANTAGES OF THE INVENTION

In view of the above, it is an object of the present invention to provide a system and a method for modifying documents, and specifically for replacing an original document portion with a substitute document portion or inserting a substitute document portion in a communications network, where the replacement decision is made based on the information content of the original document portion.

It is another object of the invention to perform this exchange operation in an efficient manner in a convenient part of the network and to allow the network user to decide which document portions should be exchanged.

Yet another object of the invention is to perform the document modification according to decisions derived from the service provider.

Still another object of the invention is the ensure that the system and method of invention can be integrated in any communications network in which content providers, service providers and users are connected via communication links (e.g., the Internet).

These and other objects and advantages will become more apparent after consideration of the ensuing description and the accompanying drawings.

SUMMARY OF THE INVENTION

The objects and advantages of the invention are ensured by a system and method applied to a communications network which transmits information in the form of documents or rather document portions, e.g., the Internet. An original document is modified to produce a modified document based on the original document portions and, specifically, based on an identifier portion and an information portion of each original document portion. A substitute document portion is inserted in the place of each undesired original document portion. The system according to the invention provides for a number of content providers whose servers transmit documents or document portions on the network. Service providers relay these document portions to a given network user, who displays them on a user set, e.g., a computer or a television set.

The system has a controller, typically a proxy server, for parsing the original document to locate the identifier portion of each of the original document portions, determining the information portion of each original document portion to identify the undesired original document portion, i.e., an original document portion which has an undesired content, and issuing a swap order the undesired original document portion is found. For instance, the undesired content may be an advertisement or a message not relevant to the information which the user desires to view on his or her user set.

A substitute document server receives the swap order and sends the substitute document portion to the controller. A swapping device or mechanism inserts the substitute document portion in place of the undesired original document portion. At this point the substitute document portion can be passed on to the user set and displayed. Depending on the communications network and user preferences, the actual display set can be a computer, a television set, or any other suitable end terminal with a display screen.

In one version of the system according to the invention the controller is located on the premises of the user, i.e., at the user's residence or at his or her work place. Advantageously, in this embodiment the controller can be integrated with the user set. It is also possible to integrate the swapping mechanism with the controller. Of course, the controller can also be located on the premises of the service provider and be integrated with the swapping mechanism there. In this situation the role of the controller and swapping mechanism can be most efficiently performed by the proxy server.

The identifier portion of any original document portion can be as simple as a network address. In general, this will be the network address of the content provider who placed the document portion on the network. (Address-based identification is one of the most common ways of identifying document portions.) The content of the information portion can be easily determined as desired or undesired from the provider's address. For this purpose, the controller should have in its memory or some other accessible storage resources a list of network addresses of content providers. In another embodiment the identifier portion will have a brief description or designation of what is contained in the information portion. Such identifier portion will generally consist of any number of signs and/or characters (usually abbreviations).

In a preferred embodiment the controller has a device or mechanism for matching the dimensions of the substitute document portion with the dimensions of the original document portion being replaced, i.e., the undesired original document portion. This provision ensures that the swapped information will be of appropriate size when rendered on the user's screen, thus preserving the page layout which would have been obtained without swapping.

A further embodiment adds to the system a user profile bank. The bank has user profile information, e.g., statistical information, personal preferences or any other information either compiled or gathered directly from the user. The profile information is delivered to the controller such that the swap order can be issued based on the user's preferences to tailor the substitute document portions to the user's needs or other relevant profile information.

The system of the invention can be used in any communications network having the general architecture described. As mentioned above, the Internet is well-suited for the system of the invention. The method of swapping undesired original document portions with substitute document portions is practiced in communications network exhibiting the same architecture as required for the system.

A detailed description of the system and method of the invention are set forth below in reference to the drawing figures.

DETAILED DESCRIPTION

Figures 1, 2:
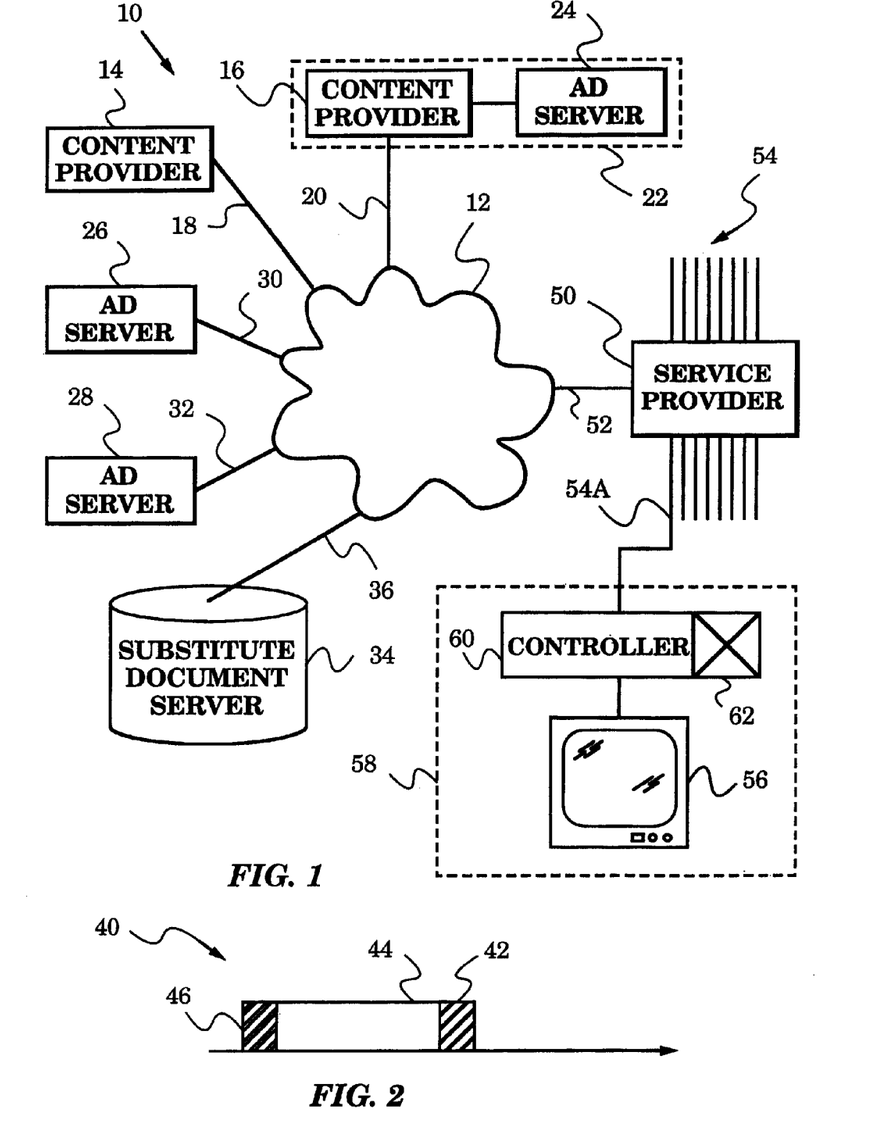
FIG. 1 is a block diagram of one embodiment of the system of invention.
FIG. 2 is a diagram of a document portion.

An advantageous embodiment of the invention is illustrated in the block diagram of FIG. 1. A document modification or swapping system 10 possessing the necessary architecture to practice the invention is built around a communications network 12. The individual links and resources of network 12 are not shown, but are generally known to include couplings, high and low bandwidth links, filters, power sources, repeaters, transformers, up- and down-converters, amplifiers and any number of other equipment required to efficiently transmit information across large physical distances. Network 12 may be a stand-alone network or one which takes advantage of existing connections and resources, e.g., telephone lines. Communication network 12 may comprise a computer network or a cable network. In the preferred embodiment network 12 is simply the Internet.

Two content providers 14, 16 are connected to network 12 via communication links 18 and 20 respectively. Any suitable medium of sufficient bandwidth to transmit the required information to and from network 12 can be used as links 18, 20. Content providers 14, 16 are servers equipped with the necessary resources to transmit and receive information, specifically requests or queries for the contents of their data banks (not shown). Typically, content providers 14, 16 have information such as articles, news briefs and updates, weather maps, books, summaries, files, software, catalogues, documents, pictorials, video files, public records, commercial literature and so forth.

Provider 14 is an independent server, while provider 16 is a part of a larger resource 22 including an advertisement server 24 (hereafter "ad server"). Although it is understood that either provider 14 or 16 may place on network 12 various types of information, e.g., requested files, non-requested information, undesired information and advertising material, the distinction between ad server 24 and provider 16 is useful for better illustrating the operation of system 10. Thus, in the present embodiment it will be assumed that ad server 24 places, via provider 16, on network 12 unsolicited information, i.e., commercials and advertisements, while provider 16 delivers requested and/or desired information.

System 10 also has dedicated ad servers 26 and 28 which deliver to network 12 via communication links 30 and 32 commercials and advertisements in the broadest sense.

A substitute document server 34 is connected with network 12 by communication link 36. Server 34 contains information which is not requested or solicited but is desirable or useful. For example, server 34 may contain health-related information, warnings, general advisories and many other types of information.

The different types of information placed on network 12 by providers 14, 16, ad servers 24, 26, 28 and substitute document server 34 are formatted in documents or document portions such as document portion 40 shown in FIG. 2. It is understood that the fundamental building blocks of document portion 40 are information packets (not shown). Although the detailed structure of document portion 40 will be adapted to network 12 each document portion 40 has the same general make-up. A header or an identifier portion 42 generally precedes an information portion 44 with the actual information content. In some cases a footer 46 may be provided to designate the end of document portion 40. Frequently, identifier portion 42 is simply the network address of the server which placed document portion 40 on network 12. Alternatively, identifier portion 42 contains a designation or identification of the information contained in portion 44. Examples of different forms which identifier portion 42 can assume when network 12 is the Internet are discussed below.

A service provider 50 is in communication with network 12 via communication link 52. Typically, service provider 50 will have numerous lines 54 connecting directly to the subscribers or network users. In particular, line 54A establishes a link between service provider 50 and a user set 56 on user premises 58. When network 12 is the Internet user set 56 is a computer or a network unit. Other devices such as television sets or display devices capable of receiving and/or sending document portion 40 can be used as well. A person of average skill in the art will be able to ensure a suitable connection of user set 56 with service provider 50.

A controller 60 is switched between user set 56 and service provider 50. Controller 60 is capable of reading identifier portion 42 of a document portion 40 to determine the content of information portion 44. A swapping device 62, preferably integrated with controller 60 as shown, is also provided to receive a swap order which controller 60 issues when information portion 42 of a packet 40 has an undesirable content.

Figure 4:
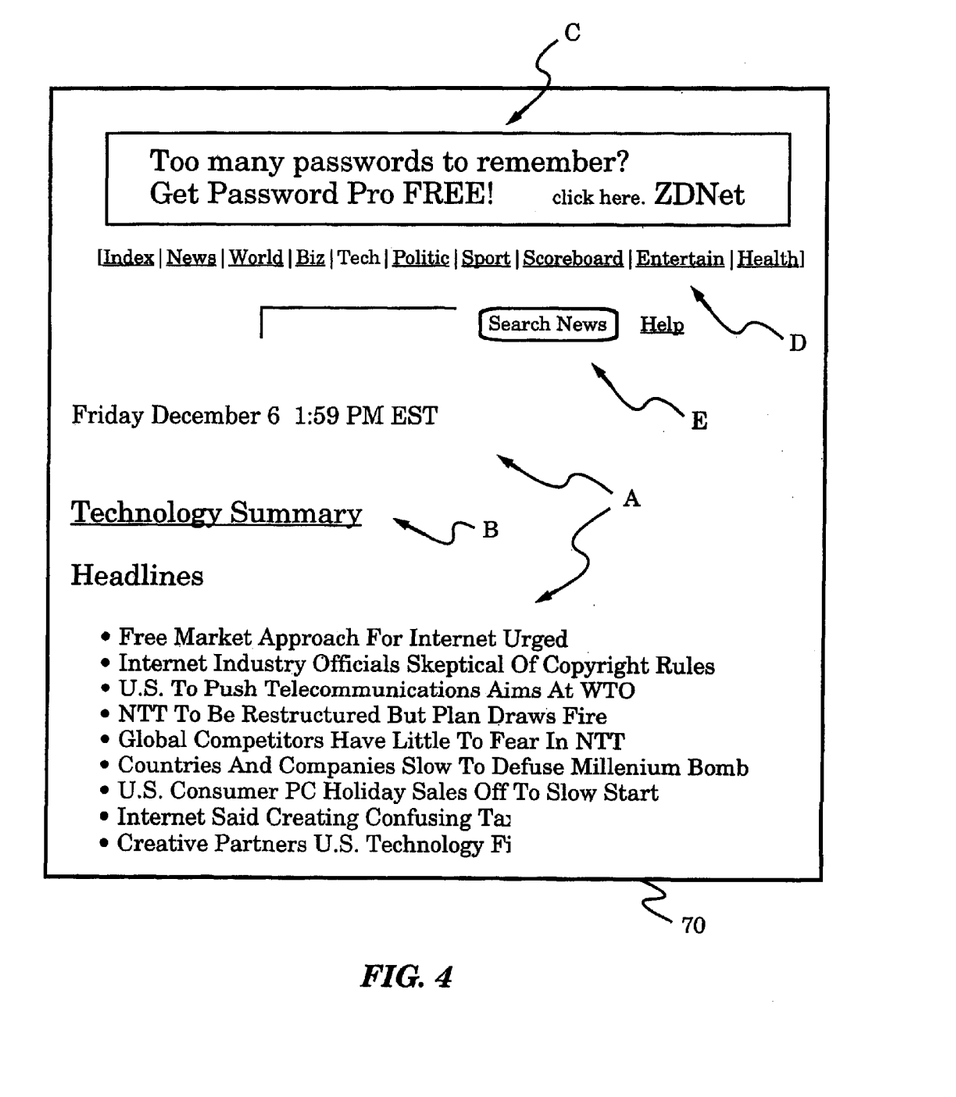
FIG. 4 is an example screen display on a user's set.

The operation of system 10 is now described for the case in which network 12 is the Internet. As an example, FIG. 4 shows a screen display or a page 70 on user set 56. Page 70 is actually constructed from a number of original document portions analogous in all respects to document portion 40. The below listing identifies how the page is rendered from original document portions A, B, C, D and E. The formats used conform to the widely accepted and well-known hypertext mark-up language (HTML).

Example Page:
HTML for Document Portion A

---

Friday December 6 1:59 PM EST
</strong>
<!-- Text Start-->
<p>
<h2><a href=/headlines/961206/tech/summary_1.html>Technology Summary</a></h2>
<hr>
<h2>Headlines</h2>
<ul>
<li><a href=/headlines/961206/tech/stories/free_1.html><b>Free Market Approach For Internet Urged</b></a>
<li><a href=/headlines/961206/tech/stories/copyright_3.html><b>Internet Industry Officials Skeptical of Copyright Rules</b></a>
<li><a href=/headlines/961296/tech/stories/telecom_1.html><b>U.S. To Push Telecommunications Aims At WTO</b></a>
<li><a href=/headlines/961206/tech/stories/ntt_1.html><b>NTT To Be Restructured But Plan Draws Fire</b></a>
<li><a href=/headlines/961206/tech/stories/nttanalysis_1.html><b> Global Competitors Have Little To Fear In NTT</b></a>
<li><a href=/headlines/961206/tech/stories/millennium_1.html><b> Countries And Companies Slow To Defuse Millennium Bomb</b></a>
<li><a href=/headlines/961206/tech/stories/sales_1.html><b>U.S. Consumer PC Holiday Sales Off To Slow Start</b></a>
<li><a href=/headlines/961206/tech/stories/taxes_1.htm><b>Internet Said Creating Confusing Tax Burden</b></a>
<li><a href=/headlines/961206/tech/stories/creative_1.html><b>Creative Partners U.S. Technology Firms</b></a>
</ul>
</body>
</html>
HTML for document portion B
<html>
<head>
<title>Technology Summary</title>
</head>
<body>
HTML for document portion C (Advertisement)
<!-- AdSpace -->
<!-- AdParam yhn000001424187 -->
<center><p><a href="http://www.yahoo.com/SpaceID=yhn00000142/AdID=4187/?http:// community.zdnet.com/register/register.cgi"><img width=460
height=55 src="http://www.yahoo.com/adv/zdi2/password5.gif"
alt="[Too many passwords to remember? Download Password Pro for free.]" border=0></a> <p></center>
<!--/AdSpace-->
HTML for document portion D (Links)
<center><strong>[
<a href=/headlines/>Index</a>|
<a href=/headlines/news/>News</a>|
<a href=/headlines/international/>World</a>|
<a href=/headlines/business/>Biz</a>|
<strong>Tech</strong>
<a href=/headlines/politics/>Politic</a>|
<a href=/headlines/sports/>Sport</a>|
<a href=http://sports.yahoo.com/>Scoreboard</a>|
<a href=/headlines/entertainment/>Entertain</a>|
<a href=/headlines/health/>Health</a>
]</strong>
</center>
<p>
HTML for document portion E (Processing User Input)
<center>
<form
method=get action="http://search.main.yahoo.com/search/news">
<hr>
<input size=24 name=p> <input type=submit value="Search News">
<input type=hidden name=n value=10>
<a href="http://www.yahoo.com/docs/info/news_search_help.html">
<small>Help</small></a><br>
</form>
</center>
<!--StartLinks-->

-continued

```
<!--EndLinks-->
<hr>
<strong>
<!-- Yahoo Time Stamp: 849898740 -->
```

In the above example original document portions A, B, C, D and E correspond to those indicated in FIG. 4. The information rendered and displayed on page 70 is of the news type and it is understood that any other type of information can be involved. Original document portion C contains an ad which originated in one of ad servers 24, 26 or 28 and was not requested by the user. Specifically, document portion C starts with identifier portion 42 indicating that the information to follow is an ad.

```
<!-- AdSpace -->
In an alternative case, identifier portion 42 can legitimately
contain:
<a href="http://www.yahoo.com/SpaceID=yhn00000142/AdID=4187/?http
:// community.zdnet.com/register/register.cgi">
```

Here, portion 42 identifies the network address of ad server (24, 26 or 28). It is clear that a number of commands is required to render document portion C. These commands relate to proper spacing, location and other parameters of document portion C. The format of these commands is commonly known and widely used, e.g., in the layout of home pages for Internet users. A person of average skill in the art will know how to interpret the commands and how they act to render document portion C on user set 56.

During operation the network user will send requests from user set 56 to service provider 50 for specific information, e.g., |Biz| in section D. Service provider 50 will, based on this request, obtain the desired information from content provider 14 or 16 (depending on which provider has the information). Of course, service provider 50 may have already downloaded the information in question. This may be the case with frequently asked for data, minute-by-minute updates, etc. In such situation provider 50 can comply with the request without looking for the information on network 12. In any case, however, the requested information originates at provider 14 or 16.

Figure 5:
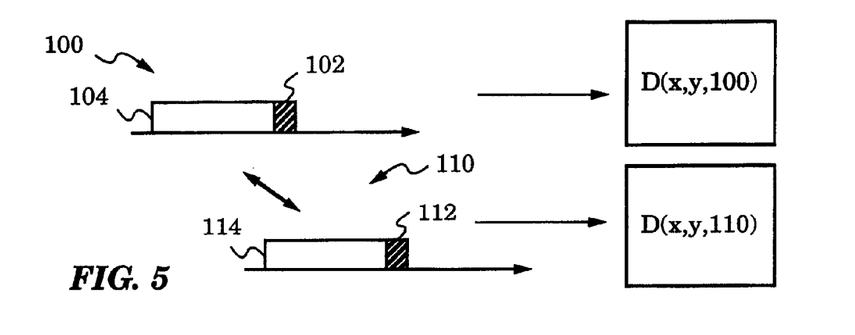
FIG. 5 is a diagrammatic representation of an original document portion and a substitute document portion.

The document as finally rendered on the screen of user set 56 thus consist of many document portion such as portion 40. As shown in FIG. 5, the specific document portion requested by the user is referred to as original document portion 100 for clarity. After original document portion 100 is obtained from provider 14 or 16 (or retrieved from the memory resources (not shown) of service provider 50) it is transmitted via line 54A to controller 60. An identifier portion 102 of original document portion 100 is read by controller 60 to determine the content of information portion 104 of original document portion 100.

As explained above, an ad from ZDNet, which is considered undesirable content, has identifier portion 102 describing the information to follow as <!--AdSpace-->. Alternatively, identifier portion 102 may simply contain the network address <a href="http://www.yahoo.com/SpaceID=yhn00000142/AdID=4187/?http://community.zdnet.com/register/register.cgi"> of ad server (24, 26 or 28, depending on which server placed the ad on network 12).

Controller 60 has properly received from user set 56 the request for |Biz|. While parsing the original document obtained as a result of the request controller 60 detects identifier portion 102 of original document portion 100 (in this case the same as document portion C described above) which contains <!--AdSpace-->. These characters distinctly signal that the information in original document portion 100 is an undesired original document portion (in this case unsolicited). Consequently, controller 60 will issue a swap order to swapping mechanism 62.

Figure 6:
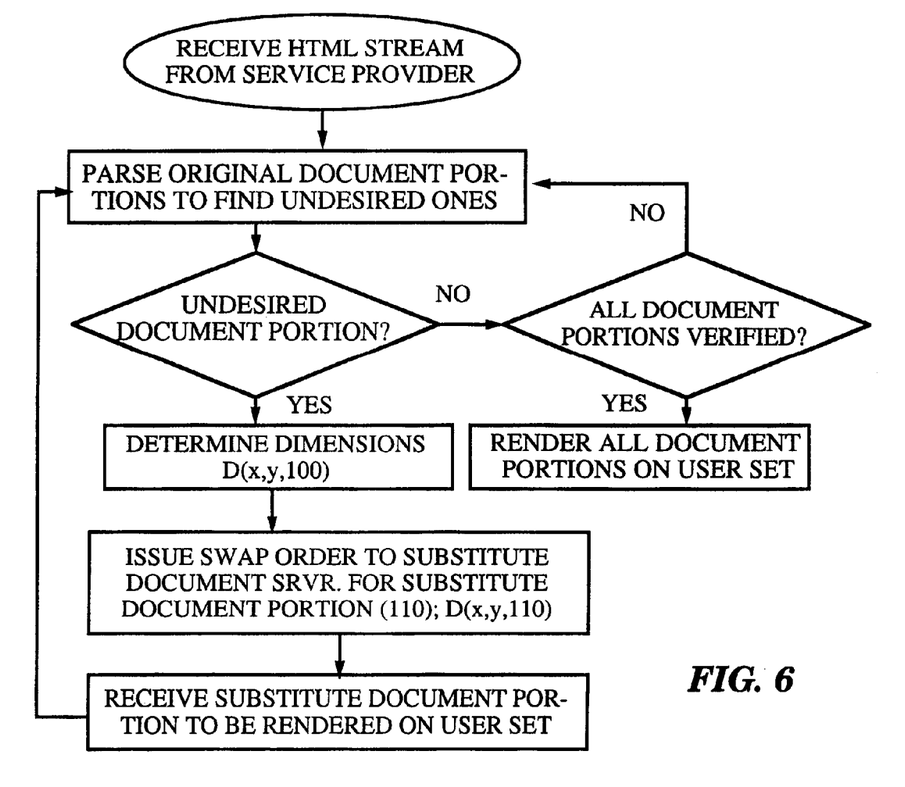
FIG. 6 is a flow diagram showing how a swap order is issued.

The swap order is formatted as any other information request (e.g., the one for |Biz|) and is addressed to substitute packet server 34. FIG. 6 shows of flow diagram detailing the steps involved in generating and issuing the swap order. It is understood that the software for executing these steps can be written by any person skilled in the art.

The swap order travels via line 54A to service provider 50 who procures the requested substitute document portion 110 (see FIG. 5) from substitute document server 34. Substitute document portion 110 has dimensions D(x,y,110) when rendered as show in FIG. 5. Preferably dimensions D(x,y,110) are close or equal to dimensions D(x,y,100) of original document portion 100. This provision will ensure that page 70 on the user set 56 will have approximately the same size as if original document portion 100 had been received and rendered on the screen of user set 56. In many cases this request can be easily satisfied since the size and width of any document portion when rendered is generally provided as a rendering hint and can be read directly from the HTML code. In the above example original document portion C includes the hint: <img width=460 height=55. In other cases controller can either fetch the content of original document portion 100 to determine the rendered size.

Alternatively, when identifier portion 102 contains the address <a href="http://www.yahoo.com/SpaceID=yhn00000142/AdID=4187/?http://community.zdnet.com/register/register.cgi"> controller 60 will be alerted that the information in original document portion 100 is undesired. That is because controller 60 keeps a list of addresses of content providers or ad servers or both. By comparing the address of portion 102 with the addresses of providers 14, 16 controller can ascertain that information portion 104 is undesirable, since the address of zdnet (one of ad servers 24, 26 or 28) is not on the list. If controller 60 is working with a list of ad servers 24, 26 or 28 it will determine that information portion 104 is undesirable when identifier portion 102 contains the address of one of ad servers 24, 26 or 28. Clearly, when using the address-based method of identifying undesirable information the address lists should be updated frequently.

At this point, controller 60 will issue a swap order, as described above, to swapping mechanism 62. The swap order will be used, as explained above, to procure substitute document portion 110 from substitute document server 34. Again, it is preferable that dimensions D(x,y,110) of substitute document portion 110 be approximately equal to dimensions D(x,y,100) of original document portion 100.

Figure 3:
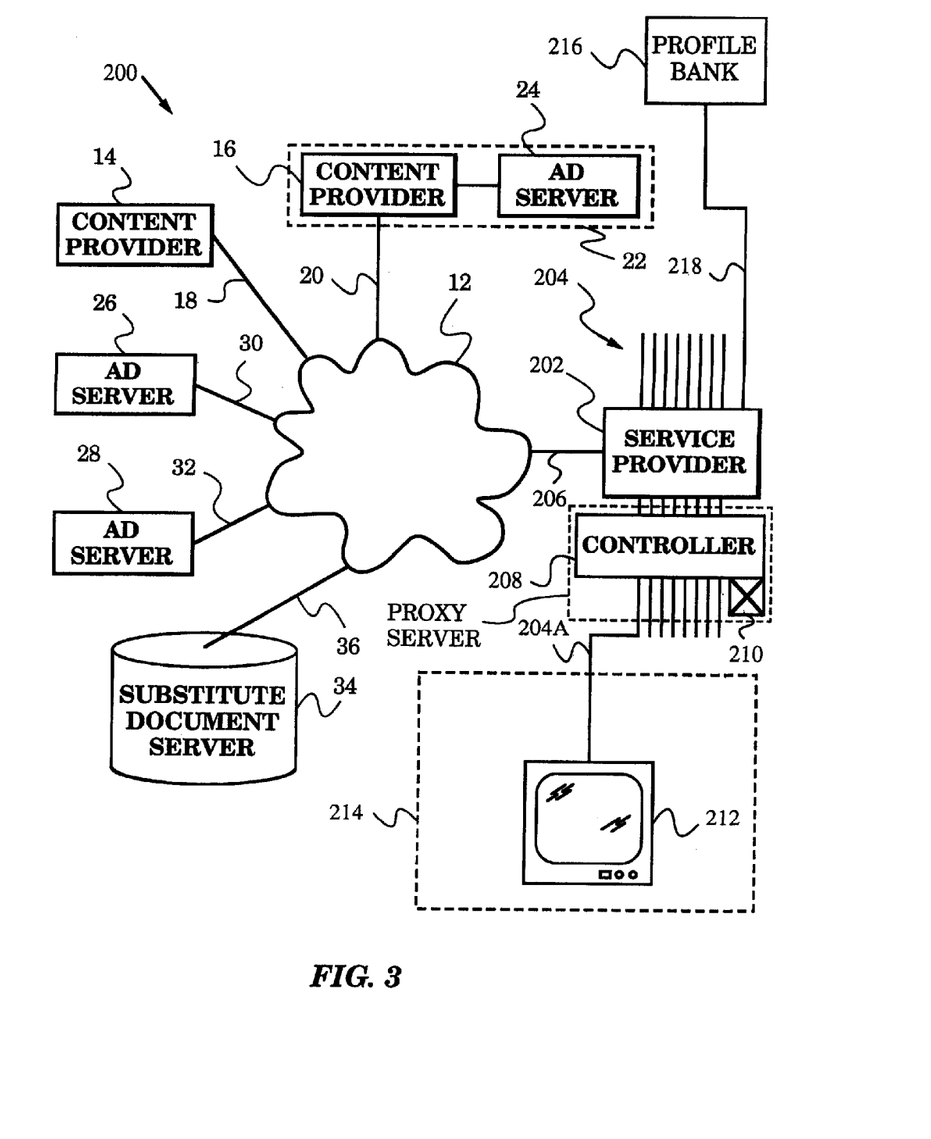
FIG. 3 is a block diagram of another embodiment of the system of invention.

Another embodiment of the invention is shown in FIG. 3. As in the first embodiment, a document modification system 200 consists of content providers 14, 16, ad servers 24, 26, 28 connected to network 12 by communication links 18, 20, 30 and 32. Substitute document server 34 is connected to network 12 by link 36.

A service provider 202 with lines 204 going out to subscribers is connected to network 12 via link 206. A controller 208, most conveniently a proxy server, is connected directly to a number of lines 204 on which the document portion swapping or insertion function is desired. Controller 208 may be integrated in the circuitry of service provider 202 or be a stand-alone unit. A swapping mechanism 210 is connected to controller 208 and, in a particularly convenient embodiment, can be integrated with the circuitry of controller 208 and service provider 202. The choice of how service provider 202, controller 208 and swapping mechanism 210 are arranged and interconnected can be determined by the circuit designer. In fact, if service provider 202 has all the necessary hardware and circuitry then the functions of controller 208 and/or swapping mechanism 210 may all be performed by service provider 202 given the appropriate software.

A particular line 204A shows the path from service provider 202 to user set 212 on user premises 214. In this embodiment no additional equipment is required of the user. This means that user set 212 is simple to install and may, for example, be a television set configured for WebTV.

A profile bank 216 is also connected via line 218 to service provider 202. Bank 216 typically contains user information such as user preferences, past activity data or even medical records. The connection with bank 216 is such that service provider 202 may request and obtain user profile information from bank 216.

The operation of this embodiment is analogous to that of the first embodiment. The difference is that the functions of parsing original document and specifically original document portions 100 and deciding whether to issue a swap order for substitute document portion 110 are performed by service provider 202. In addition, when issuing the swap order, swapping mechanism 210 may take into account the profile of the user obtained from bank 216.

For example, data bank 216 may contain the medical records indicating that the user is a diabetic and should be reminded to monitor their blood glucose level. In this situation, when original document portion 100 is undesired, swapping mechanism 210 will issue a swapping order addressed to substitute document server 34 to provide a substitute document portion 110 in which information portion 114 contains the message "remember to monitor your blood glucose level". In the event the user is trying to quit smoking, substitute document portion 110 may contain the following message: "Don't give up! You can quit smoking!".

Figure 7:
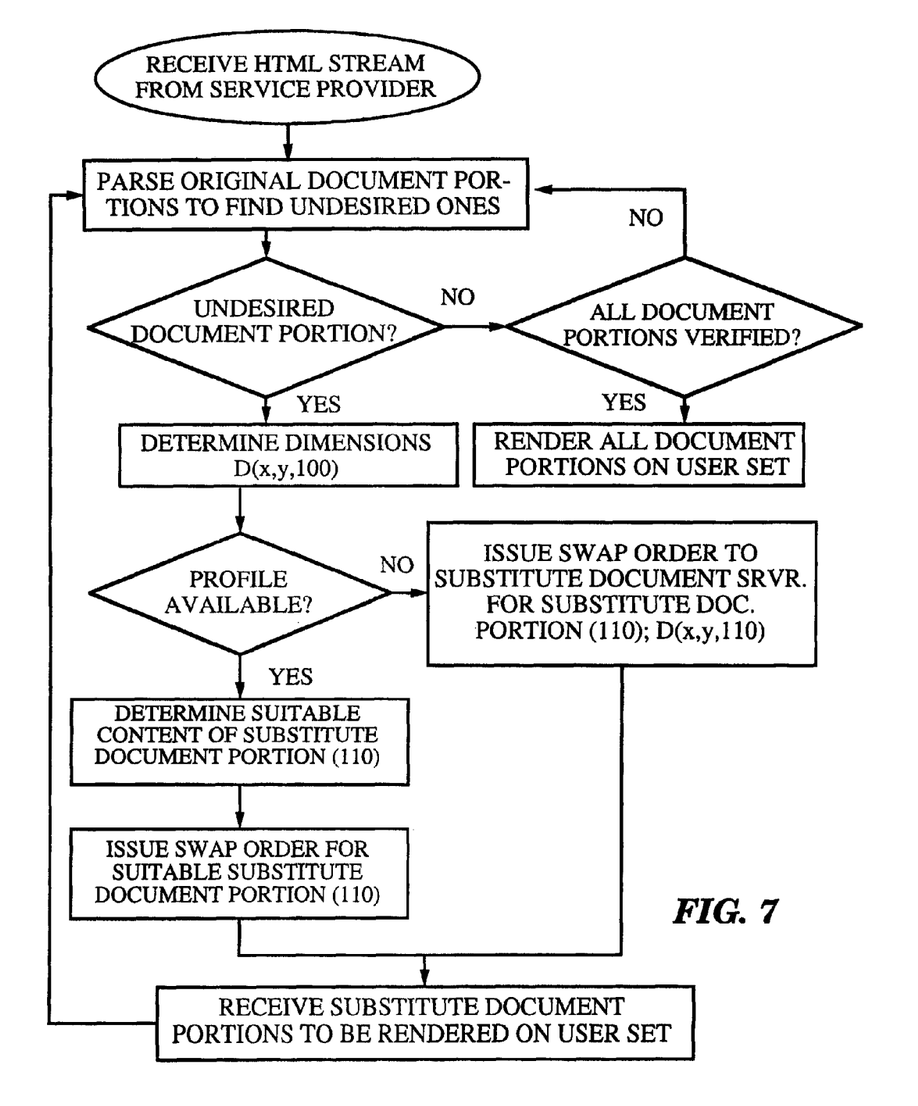
FIG. 7 is a flow diagram showing how a swap order is issued when profile bank information is available.

FIG. 7 shows in flow diagram format how the swap order is generated and issued. Swapping mechanism 210 and controller 208 will perform these steps with the aid of conventional software steps which can be programmed by a person skilled in the art.

In a preferred embodiment of the invention system 10 is used in conjunction with a browser software installed on user set 56. Browsers are well-known and commonly used to communicate on the Internet. Examples of suitable browsers include the Netscape Navigator© supplied by Netscape, Inc. and Internet Explorer© provided by Microsoft, Inc. The operation of all components is as described above with the difference that the browser software performs the function of controller 60 and swapping mechanism 62 according to the diagram of FIG. 6.

For example, the user may wish to be updated on the local news rather than receive advertisements. In this case the user will select under the options "what to swap" to receive information content 114 concerning local news.

Alternatively, the user may wish to be reminded of other important personal information. For example, the user may have asthma. He or she will then select substitute document portion 110 to contain a reminder to take their respiratory peak flow reading or appropriate medication. Clearly, the information can be tailored to any user according to need. To offer these options substitute document server 34 has to be loaded with the appropriate information.

Figure 8:
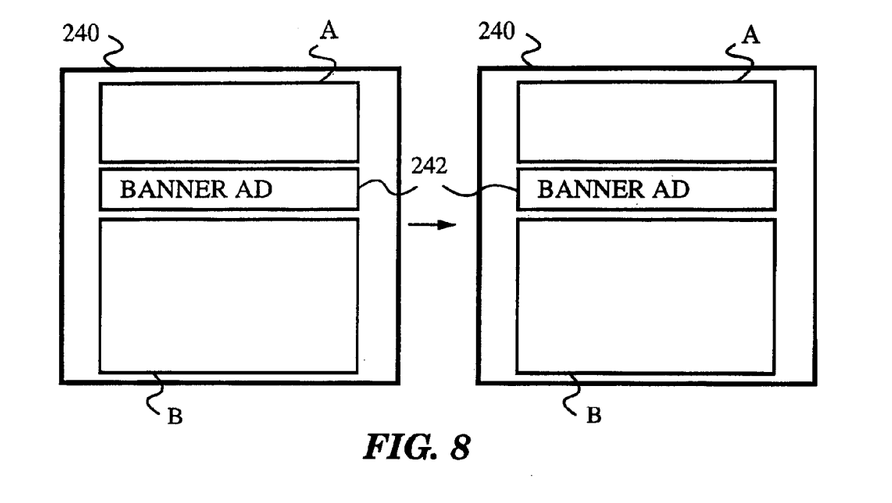
FIG. 8 is a diagram illustrating typical placement of undesired original document portions on a page.
Figure 9:
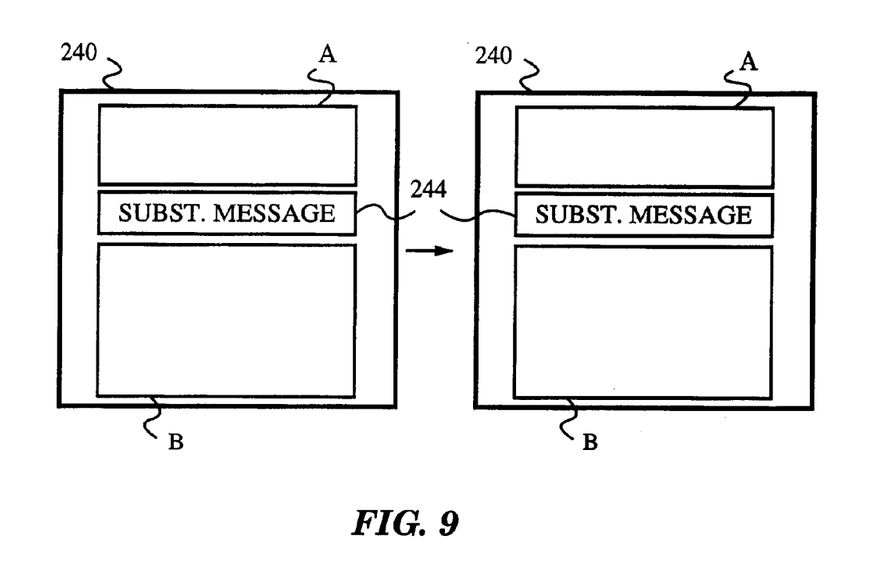
FIG. 9 is a diagram illustrating the replacement of undesired original document portions with specified substitute document portions.

In a particularly advantageous embodiment of the invention the browser can be instructed to replace all banner ads. These ads are located using the techniques discussed above. Two typical web pages 240 with banner ads 242 are shown in FIG. 8. Ads 242 are located in the middle of each page 240 between sections A and B. The browser will easily recognize and swap these ads with substitute document portions which render to messages 244 as shown in FIG. 9.

In an embodiment adapted to current practice controller 60, 208 can even determine where an address of an identifier 102 is directed to by going to that address. This has to be done when ad servers require the user to "click" on them to go to a web page which describes the item. In most cases the "click-through" web page is hosted on a different service. As the page is being rendered, controller 60, 208 operating according to the method of the invention can determine where each HREF instruction goes by looking up network addresses as registered in the Domain Network Server (DNS). An HREF which is part of an image that is associated with a different address than the source HTML from content provider 14, 16 is usually an advertisement.

Many ad services keep track of "click-through" rates. This is done by aliasing an address on the current service which bounces the click to the target address. In this way the service can count how often the alias was used. The method of invention can be adapted to this situation in two ways.

According to a first strategy, the reference can be identified by making an HTTP request from the HREF address and then looking at the reply address. If a redirect to another site is discovered then the document portion most likely contains an advertisement.

A second strategy is to parse the HREF string. In the listing shown above the redirect address contained in original document portion C is easy to find; it is: href="http://www.yahoo.com/SpaceID=yhn00000142/AdID=4187/?http://community.zdnet.com/register/register.cgi">. Although the request is part of the "yahoo.com" address, the redirect goes to "community.zdnet.com". A DNS lookup of this address reveals that it belongs to a different service and that document portion C is an ad.

Finally, the swapping function according to the invention can be used as an insert function. For example, if original document portion 100 contains a blank, controller 60, 208 can send a request for substitute document portion 110 to fill this blank. In this manner the space on the rendered page is more completely and efficiently utilized.

SUMMARY, RAMIFICATIONS, AND SCOPE

Although the above description contains many specificities, these should not be construed as limitations on the scope of the invention but merely as illustrations of the presently preferred embodiment. Many other embodiments of the invention are possible. For example, the functionality of the controller and swapper may reside in software installed on the service provider's resources. Alternatively, software resident in the user set may cooperate with software in the service provider's resources to provide the functionality of the controller and swapping mechanism.

Therefore, the scope of the invention should be determined not by the examples given but by the appended claims and their legal equivalents.

The invention claimed is:

1. A system for generating documents, said system comprising:
   a first computer configured as a first server to provide a first content to be sent over at least one communication network;
   a second computer configured as a second server to provide a second content to be sent over the at least one communication network; and
   a third computer configured to (i) request said first content from said first server, (ii) identify substitutable portions of said first content and determine first dimensions said substitutable portions would have had if rendered on a screen of a user by parsing said first content received from said first server, (iii) request said second content from said second server using a swap order including second dimensions, wherein the second dimensions are defined using the first dimensions, wherein said second content has predefined third dimensions and is selected based upon the second dimensions, such that the second content has a size that when rendered on the screen of the user preserves a page layout that would have been obtained without swapping the second content for the substitutable portions of the first content, (iv) insert said selected second content received from said second server in place of at least one of said substitutable portions in said first content, and (v) display said first content as modified by the insertion of said second content.

2. The system according to claim 1, further comprising:
   a service provider coupled to said first server, wherein said service provider is configured to obtain said first content from said first computer in response to said request from said third computer.

3. The system according to claim 1, wherein said third computer is part of a proxy server.

4. The system according to claim 1, wherein said first content comprises hyper-text mark-up language (HTML).

5. The system according to claim 4, wherein said hyper-text mark-up language (HTML) comprises code for one or more types of content selected from the group consisting of home pages of companies, home pages of organizations, internet directories, sports news pages and stock quotation pages.

6. The system according to claim 1, wherein one or more of said documents are generated by removing one or more substitutable portions in said first content.

7. The system according to claim 1, wherein at least one of said substitutable portions is replaced by an advertisement having a size that is similar to a size of the at least one substitutable portion when rendered on a display screen.

8. The system according to claim 7, wherein said advertisement comprises (i) automatically changing content or (ii) content based on said first content.

9. The system according to claim 1, wherein at least one of said substitutable portions is replaced with health-related material having a size that is similar to a size of the at least one substitutable portion when rendered on a display screen.

10. The system according to claim 9, wherein the health-related material is obtained from one or more sources selected from the group consisting of a profile bank, medical records and a health content server.

11. The system according to claim 1, wherein at least one of said substitutable portions is replaced with material comprising one or more types of data selected from the group consisting of video, audio, hyper-text mark-up language (HTML) and text-to-speech data.

12. The system according to claim 1, wherein said substitutable portions comprise one or more blank portions and one or more of said documents are generated by inserting material from said second content into said one or more blank portions of said first content.

13. The system according to claim 12, wherein the material inserted comprises (i) an advertisement or (ii) health-related material having a size that is similar to a size of the one or more blank portions when rendered on a display screen.

14. The system according to claim 13, wherein the health-related material is obtained from one or more sources selected from the group consisting of a profile bank, medical records and a health content server.

15. The system according to claim 1, wherein one or more documents are generated by adding material to said first content.

16. The system according to claim 15, wherein the material added comprises an advertisement.

17. The system according to claim 15, wherein the material added comprises health-related material.

18. The system according to claim 1, wherein said second computer is further configured to personalize said second content using profile data.

19. The system according to claim 18, wherein said profile data comprises one or more types of data selected from the group consisting of a medical treatment regimen, a health profile, an educational treatment plan, a psychological profile and a patient history.

20. The system according to claim 19, wherein said psychological profile comprises one or more types of information selected from the group consisting of (i) information gathered from tests of a patient, (ii) information gathered from questionnaires and (iii) information gathered by monitoring usage of the system.

21. The system according to claim 20, wherein said information gathered by monitoring usage of the system is gathered by recording subjects corresponding to material clicked on.

22. The system according to claim 18, wherein said second content is limited using said profile data.

23. The system according to claim 1, wherein said third computer is configured to identify the substitutable portions of said first content using a network address associated with the substitutable portions.

24. The system according to claim 1, wherein said third computer is configured to identify the substitutable portions of said first content and determine fourth dimensions of the first content using an identifier portion.

25. The system according to claim 1, wherein said substitutable portions comprise one or more portion types selected from the group consisting of un-desired portions, un-used portions, blank portions and portions targeted for replacement.

26. The system according to claim 1, wherein said at least one communication network comprises a computer network.

27. The system according to claim 1, wherein said at least one communication network comprises a cable network.

28. The system according to claim 1, further comprising a profile bank configured to provide profile information.

29. The system according to claim 28, wherein said profile bank is coupled to said second computer.

30. The system according to claim 28, further comprising a service provider coupled to said first computer and said profile bank, wherein said service provider is configured to obtain said first content from said first computer in response to a request from said third computer and swap one or more of said substitutable portions based on said profile information.

31. The system according to claim 28, wherein said profile information comprises health-related material.

32. The system according to claim 28, wherein said profile information comprises one or more types of data selected from the group consisting of statistical information, personal preferences, past activity information and medical records.

33. The system according to claim 28, wherein said profile bank comprises an electronic medical records system.

34. The system according to claim 28, wherein said profile information comprises information either compiled or gathered directly from an individual.

35. The system according to claim 28, wherein said third computer is further configured to tailor the substitutable portions based on the profile information.

36. The system according to claim 1, wherein said second content comprises hyper-text mark-up language based on said first content.

37. The system according to claim 1, wherein said second content comprises one or more advertisements based on said first content.

38. The system according to claim 1, wherein said first content is displayed by a web browser.

39. The system according to claim 1, wherein said third computer is configured as a third server.

* * * * *